US012797155B2

(12) United States Patent
Park et al.

(10) Patent No.: US 12,797,155 B2
(45) Date of Patent: Nov. 17, 2026

(54) ILLUMINATION SYSTEM FOR SURGICAL MICROSCOPE WITH TUNABLE COAXIAL AND OBLIQUE BEAMS

(71) Applicant: Alcon Inc., Fribourg (CH)

(72) Inventors: John Park, Irvine, CA (US); Ronald T. Smith, Irvine, CA (US)

(73) Assignee: Alcon Inc., Fribourg (CH)

( * ) Notice: Subject to any disclaimer, the term of this patent is extended or adjusted under 35 U.S.C. 154(b) by 377 days.

(21) Appl. No.: 18/480,612

(22) Filed: Oct. 4, 2023

(65) Prior Publication Data

US 2024/0115345 A1 Apr. 11, 2024

Related U.S. Application Data

(60) Provisional application No. 63/378,492, filed on Oct. 5, 2022.

(51) Int. Cl.

| | |
|---|---|
| ***G02B 21/00*** | (2006.01) |
| ***A61B 3/13*** | (2006.01) |
| ***A61B 90/30*** | (2016.01) |
| ***G02B 21/06*** | (2006.01) |
| ***G02B 21/36*** | (2006.01) |

(52) U.S. Cl.

CPC ................ *A61B 90/30* (2016.02); *A61B 3/13* (2013.01); *G02B 21/0012* (2013.01); *G02B 21/06* (2013.01); *G02B 21/361* (2013.01); *A61B 2090/306* (2016.02)

(58) Field of Classification Search

CPC ..... A61B 90/30; A61B 3/13; A61B 2090/306; A61B 3/14; A61B 3/0008; G02B 21/0012; G02B 21/06; G02B 21/361; G02B 21/18; G02B 21/0092; G02B 21/082

See application file for complete search history.

(56) References Cited

U.S. PATENT DOCUMENTS

| | | | | |
|---|---|---|---|---|
| 9,265,458 | B2 * | 2/2016 | Stack | A61B 5/162 |
| 10,251,783 | B2 * | 4/2019 | Chernyak | A61F 9/00806 |
| 10,545,325 | B2 * | 1/2020 | Kuster | A61B 3/152 |
| 11,154,378 | B2 * | 10/2021 | Tesar | A61B 1/00193 |
| 11,957,521 | B2 * | 4/2024 | Neta | A61B 3/13 |
| 12,392,724 | B2 * | 8/2025 | Suzuki | G01N 21/6456 |
| 2004/0227989 | A1 * | 11/2004 | Obrebski | G02B 21/20 359/388 |
| 2005/0117209 | A1 * | 6/2005 | Moller | G02B 21/0012 359/368 |
| 2012/0092615 | A1 * | 4/2012 | Izatt | A61B 3/102 351/205 |
| 2022/0031511 | A1 * | 2/2022 | Charles | A61F 9/00825 |

* cited by examiner

*Primary Examiner* — Mustak Choudhury

(57) ABSTRACT

A surgical microscope is configured to capture images of an eye of a patient and defines an optical axis. An illumination source is configured to emit a plurality of beams onto the eye of the patient at a plurality of angles relative to the optical axis. A controller is coupled to the surgical microscope and the illumination source, the controller configured to independently control values for illumination parameters for each beam of the plurality of beams to facilitate imaging of the eye of the patient. The illumination parameters may compensate for reflections from the iris, offset of the eye relative to the optical axis, and reflections of ambient light. The illumination parameters may be controlled subject to inputs received from a surgeon or other user.

20 Claims, 9 Drawing Sheets

ILLUMINATION SYSTEM FOR SURGICAL MICROSCOPE WITH TUNABLE COAXIAL AND OBLIQUE BEAMS

RELATED APPLICATIONS

This application claims the benefit of U.S. Provisional Application Ser. No. 63/378,492, filed Oct. 5, 2022, and entitled COLOR TUNABLE COAXIAL AND OBLIQUE ILLUMINATION FOR OPHTHALMIC MICROSCOPY, which is hereby incorporated herein by reference in its entirety.

BACKGROUND

The present disclosure relates generally to performing ophthalmic surgery.

Light received by the eye is focused at the back of the eye, which includes the retina. The area between the cornea and the lens is known as the anterior segment. The interior of the eye between the lens and the retina is known as the posterior segment and is filled with a transparent gel known as the vitreous. Many ocular pathologies may be treated by performing ophthalmic treatments in the interior or posterior segment.

It would be an advancement in the art to facilitate the performance of ophthalmic treatments.

SUMMARY

Aspects of the present disclosure include a surgical microscope configured to capture images of an eye of a patient and defining an optical axis. An illumination source is configured to emit a plurality of beams onto the eye of the patient at a plurality of angles relative to the optical axis. A controller is coupled to the surgical microscope and the illumination source, the controller configured to independently control values for illumination parameters for each beam of the plurality of beams to facilitate imaging of the eye of the patient.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is noted, however, that the appended drawings illustrate only some aspects of this disclosure and the disclosure may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure will now be described in detail with reference to the drawings, which are provided as illustrative examples of the disclosure so as to enable those skilled in the art to practice the disclosure. Notably, the figures and examples below are not meant to limit the scope of the present disclosure to a single embodiment, but other embodiments are possible by way of interchange of some or all of the described or illustrated elements. Moreover, where certain elements of the present disclosure can be partially or fully implemented using known components, only those portions of such known components that are necessary for an understanding of the present disclosure will be described, and detailed descriptions of other portions of such known components will be omitted so as not to obscure the disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly (i.e., through one or more intermediate parts or components, so long as a link occurs). As used herein, "directly coupled" means that two elements are directly in contact with each other. As used herein, "fixedly coupled" or "fixed" means that two components are coupled so as to move as one while maintaining a constant orientation relative to each other. As used herein, "operatively coupled" means that two elements are coupled in such a way that the two elements function together. It is to be understood that two elements "operatively coupled" does not require a direct connection or a permanent connection between them. As utilized herein, "substantially" means that any difference is negligible, such that any difference is within an operating tolerance that is known to persons of ordinary skill in the art and provides for the desired performance and outcomes as described in the embodiments described herein. Descriptions of numerical ranges are endpoints inclusive.

In the exemplary embodiments described herein, an embodiment showing a singular component should not be considered limiting; rather, the disclosure is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present disclosure encompasses present and future known equivalents to the known components referred to herein by way of illustration.

Figure 1:
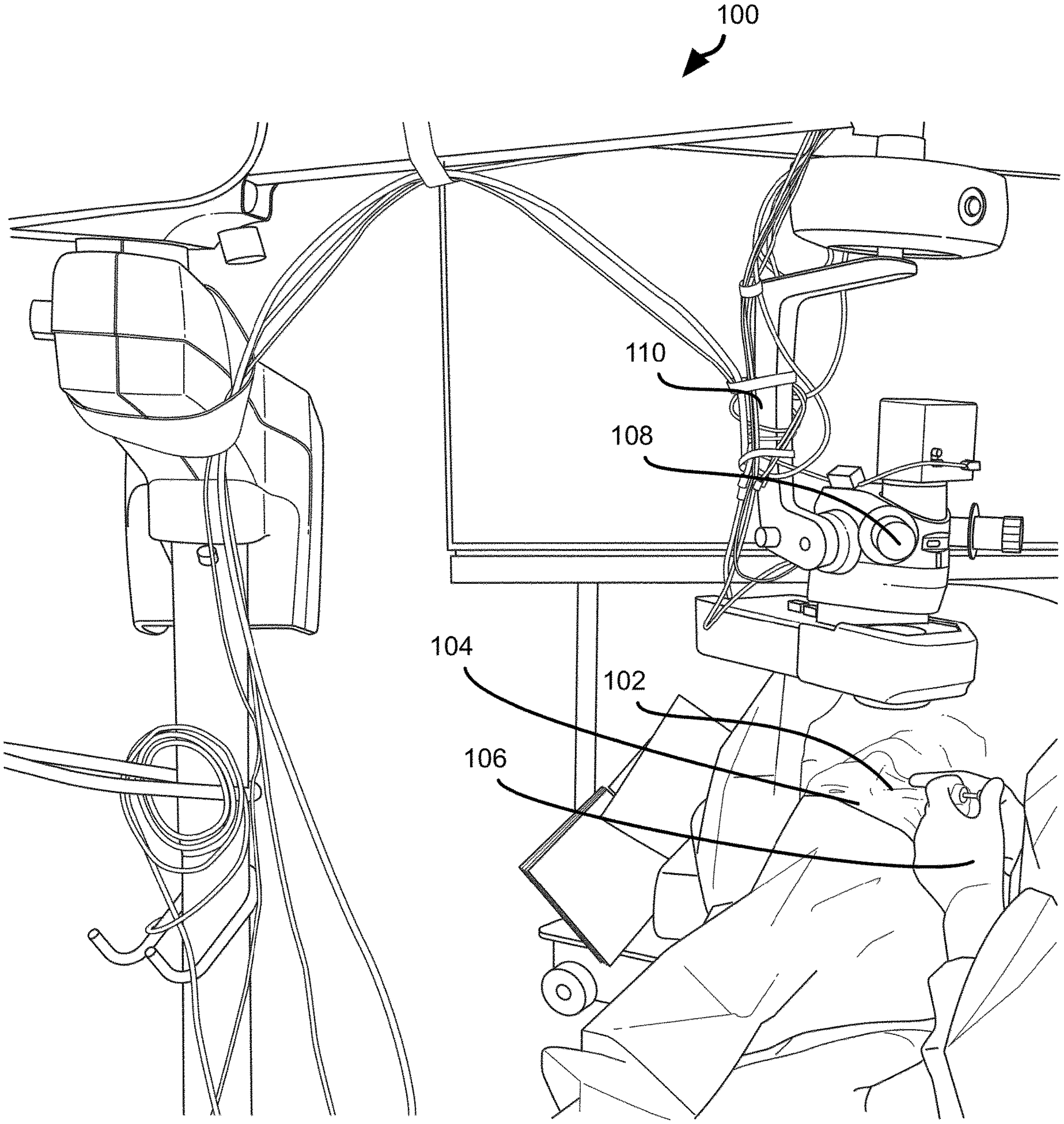
FIG. 1 illustrates a surgical microscope that may use a tunable illumination source in accordance with certain embodiments.

Referring to FIG. 1, an operating environment 100 may be used to perform an ophthalmic treatment on an eye 102 of a patient 104 by a surgeon 106. The operating environment 100 may include a surgical microscope 108 suspended from a support 110 facilitating positioning of the surgical microscope 108 over the eye 102 at a height desired by the surgeon 106. For example, surgical microscope 108 may be implemented as the NGENUITY 3D VISUALIZATION SYSTEM provided by Alcon Inc. of Fort Worth Texas.

Figure 2:
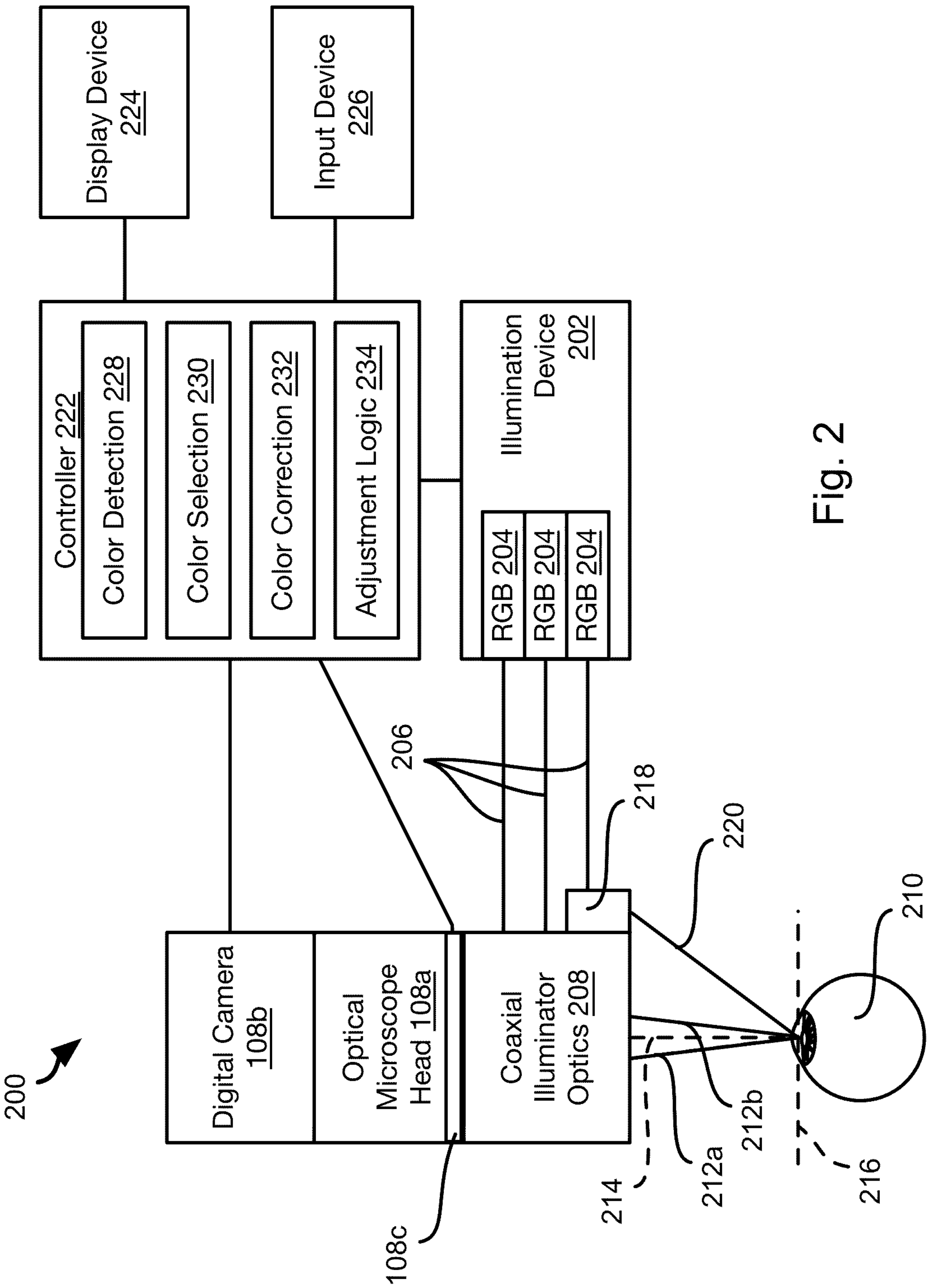
FIG. 2 illustrates components of the tunable illumination source in accordance with certain embodiments.

Referring to FIG. 2, a tunable illumination source 200 may be incorporated in or mounted to the surgical microscope 108 in order to provide illumination during an ophthalmic treatment according to some or all of the methods disclosed herein. The tunable illumination source 200 includes illumination device 202 including one or more light emitters 204. For example, in the illustrated embodiment, the tunable illumination source 200 includes a plurality of light emitters 204. Each light emitter 204 may emit light in a plurality of colors. For example, each light emitter 204 may be implemented as a set of red, green, and blue (RGB) light emitters capable of emitting a range of colors in the visible spectrum. The light emitters 204 may be coupled by one or more optical fibers 206, or bundles of optical fibers 206, to a coaxial illuminator optics 208. As used herein, red light may be understood as having a wavelengths of between 600 and 700 nm, green light may be understood as having a wavelengths of between 500 and 600 nm, and blue light may be understood as having wavelengths between 400 and 500 nm.

The coaxial illuminator optics 208 include optical components enabling light reflected from an eye 210 to pass through the coaxial illuminator optics 208 to reach an optical microscope head 108*a* and be detected using the digital camera 108*b* of the surgical microscope 108. A polarization filter 108*c* may be positioned at some point within an optical path between the eye 210 and the digital camera 108*b*. The polarization filter 108*c* may alter the polarization angle thereof in response to inputs from the controller 222 and may be turned on and off.

The coaxial illuminator optics 208 further receive light from the light emitters 204 and redirect at least a portion of the received light into coaxial beams 212*a*, 212*b* directed onto the eye 210. As used herein, "coaxial" refers to beams emitted at an angle that is within 4 degrees, 3 degrees, or 2 degrees of the optical axis 214 of the optical microscope head 108*a*, which may include a projection of the optical axis 214 through the coaxial illuminator optics 208. The coaxial illuminator optics 208 may combine an optical path of light reflected from the eye with the optical path of the coaxial beams 212*a*, 212*b*, such as by means of beam splitters, mirrors, or other optical elements.

The coaxial beams 212*a*, 212*b* may be positioned and oriented to augment the "red reflex" from the eye during cataract surgery. During an ophthalmic treatment, such as cataract surgery, red and near infrared light incident on the retina will result in a red glow from the retina that illuminates structures of the eye and is very helpful to the surgeon 106. For example, exit pupils of the coaxial illuminator optics 208 may be substantially laterally aligned with the entrance pupils of the surgical microscope 108, e.g., laterally aligned in a plane including centers of the coaxial beams 212*a*, 212*b* and the optical axis 214. From the perspective of the eye 210 of the patient looking up at the surgical microscope 108, the exit pupils of the coaxial illuminator optics may appear as two circular disks from which the coaxial beams 212*a*, 212*b* are emitted. The two entrance pupils of the surgical microscope 108 may be defined by two physical apertures that are typically located just above the objective lens of the optical microscope head 108*a*. From the perspective of the eye 210 looking up at the surgical microscope 108, the entrance pupils would appear as two dark circular disks, which are the images of the two apertures viewed through the objective lens. Therefore, the position and orientation of the coaxial beams 212*a*, 212*b* may be selected such that, from the perspective of the eye 210, two coaxial illumination exit pupils and the two microscope entrance pupils are visible. The position and orientation of the coaxial beams 212*a*, 212*b* may be selected such that the two sets of pupils are substantially (e.g., 90%) if not totally laterally overlapped, i.e., one exit pupil of one coaxial beam 212*a* (e.g., on a left side) aligned with one entrance pupil of the surgical microscope 108 (e.g., also on the left side) and the other exit pupil of the other coaxial beam 212*b* (e.g., on a right side on an opposite side of the optical axis 214 from the left side) aligned with the other entrance pupil of the surgical microscope 108 (e.g., also on the right side). The microscope entrance pupils typically have diameters of 16 mm and typically have center-to-center separations of 22 mm. The exit pupils of the coaxial beams 212*a*, 212*b* may be similarly configured, e.g., diameters of from 12 to 18 mm and center-to-center separation of between 20 and 25 mm.

The central axis of the coaxial beams 212*a*, 212*b* may converge toward one another as shown in FIG. 2 or may be parallel to one another and the optical axis 214. The amount of overlap of the coaxial beams 212*a*, 212*b* in a corneal plane 216 may be up to 100% or as small as 30%. As used herein, a percentage of overlap of beams may refer to percentage overlap of beam area, with the area of each beam defined as a region having an intensity above 50% of the maximum intensity of the beam, e.g., intensity at the center of the beam. The corneal plane 216 may be defined as a plane intersecting the limbus of the eye 210. The degree of overlap may be selected based on a tradeoff between (a) a high percentage of overlap providing a large amount of red reflex and therefore more light entering the entrance pupils of the surgical microscope 108 and (b) a smaller percentage of overlap providing illumination and corresponding red reflex over a large range of eye positions as discussed below with respect to FIGS. 7, 8, and 9. Accordingly, for embodiments implementing the approach of FIGS. 7, 8, and 9 a smaller overlap may be used, such as less than 50%. For example, for embodiments implementing the approach of FIGS. 7, 8, and 9, the coaxial beams 212*a*, 212*b* may be parallel to one another and to the optical axis 214. For other embodiments, described herein, the degree of overlap may not be as important and may be between 30% and 100%. One or more of the light emitters 204 may be coupled to oblique optics 218. The oblique optics 218 direct an oblique beam 220 at the eye 210. The center of the oblique beam 220 may be substantially aligned with the optical axis 214 in the corneal plane 216, such as within 5 mm.

In some embodiments, the position and orientation of the oblique beam 220 may be selected to reduce the red reflex induced by the oblique beam 220. In particular, an exit pupil of the oblique optics 218 may be offset from the entrance pupils of the surgical microscope 108. For example, an edge of the exit pupil of the oblique optics 218 that is closest to the microscope entrance pupils may be separated from the closest entrance pupil (the right entrance pupil in the illustrated embodiment) by at least 5 mm to essentially eliminate the red reflex induced by the oblique beam 220. However, the angle of the oblique beam 220 relative to the optical axis 214 may be limited by a desire to (1) avoid the lateral elongation of the projection of the circular oblique beam 220 onto the corneal plane 216 and (2) to avoid lateral separation between the area in the corneal plane 216 illuminated by the oblique beam 220 and coaxial beams 212*a*, 212*b*, which, in most applications, will be between 175 mm and 200 mm from the exit pupils of the coaxial illuminator optics 208 and oblique illuminator optics 218. However, mechanical limitations may demand that the oblique beam 220 define some non-zero angle with respect to the optical axis 214. For example, the oblique beam 220 may define an angle with respect to the optical axis 214 of between 5 and 12 degrees, between 7 and 10 degrees, between 7 and 9 degrees, or about 8 degrees, with a typical angle of about 8 degrees.

In the following example embodiments, two coaxial beams 212*a*, 212*b* and a single oblique beam 220 are used. It shall be understood that more than two coaxial beams 212*a*, 212*b* defining more than two angular orientations relative to the optical axis 214 may be used in a like manner. Likewise, more than one oblique beams 220 with more than one angular orientations relative to the optical axis 214 may also be used in a like manner.

A controller 222 may be coupled to the illumination device 202 to control operation of the illumination device 202. The controller 222 may further be coupled to the digital camera 108*b* in order to receive images from the digital camera 108*b* or possibly control operation of the digital camera 108*b*. The controller 222 may further be coupled to a display device 224. The display device 224 may be a display device within the surgical microscope, which may be a binocular display device. The display device 224 may also be a separate display device present in the operating environment 100 and viewable by the surgeon 106.

The controller 222 may be coupled to an input device 226. The input device 226 may be implemented as one or more physical buttons, one or more foot pedals, a touch screen, a pointing device (e.g., mouse or track pad), microphone for receiving voice commands, one or more cameras for detecting gestures, or some other input device. The controller 222 may control operation of itself and the illumination device 202 according to inputs received from the input device 226. In addition, any of the functions ascribed herein to the controller 222 may be invoked manually by the surgeon or other user through the input device 226. In particular, a surgeon may be provided with sliders for selecting intensity of each beam 212*a*, 212*b*, 220, the intensity of each color of each beam 212*a*, 212*b*, 220 or varying other parameters defining the performance of any of the methods described herein.

The controller 222 may be configured to perform various functions with respect to the illumination device 202 and images received from the digital camera 108*b*. For example, the controller 222 may include a color detection module 228 configured to analyze the color composition of pixels in images received from the digital camera 108*b* relative to the parameters of light emitted by the illumination device 202 at the time the images were captured. The controller 222 may include a color selection module 230 configured to select the color and intensity output by each light emitter 204. The controller 222 may include a color correction module 232 configured to change the color composition of images received the output of the color detection module 228.

For example, the color selection module 230 may select the color of light emitted from the light emitters 204 that has a combined intensity of blue light at a first level selected to maintain phototoxicity below a required level. The color correction module 232 may then process images received from the digital camera 108*b* in order to increase the intensity of the blue component of pixels to simulate illumination with a combined intensity of blue light at a second level that is higher than the first level. In this manner, the phototoxicity to which the eye 210 is exposed is reduced while approximating the same visibility of features of the eye expected by the surgeon 106.

In another example, the color selection module may select the color and intensity of light emitted by the light emitters 204 in order to improve the dynamic range of images captured using the digital camera 108*b*, e.g., avoid under or over saturation.

The controller 222 may include adjustment logic 234 configured to adjust color and intensity of light emitted by the illumination device 202 based on various criteria, such as according to any of the methods described below with respect to FIGS. 3 through 12.

Figure 3:
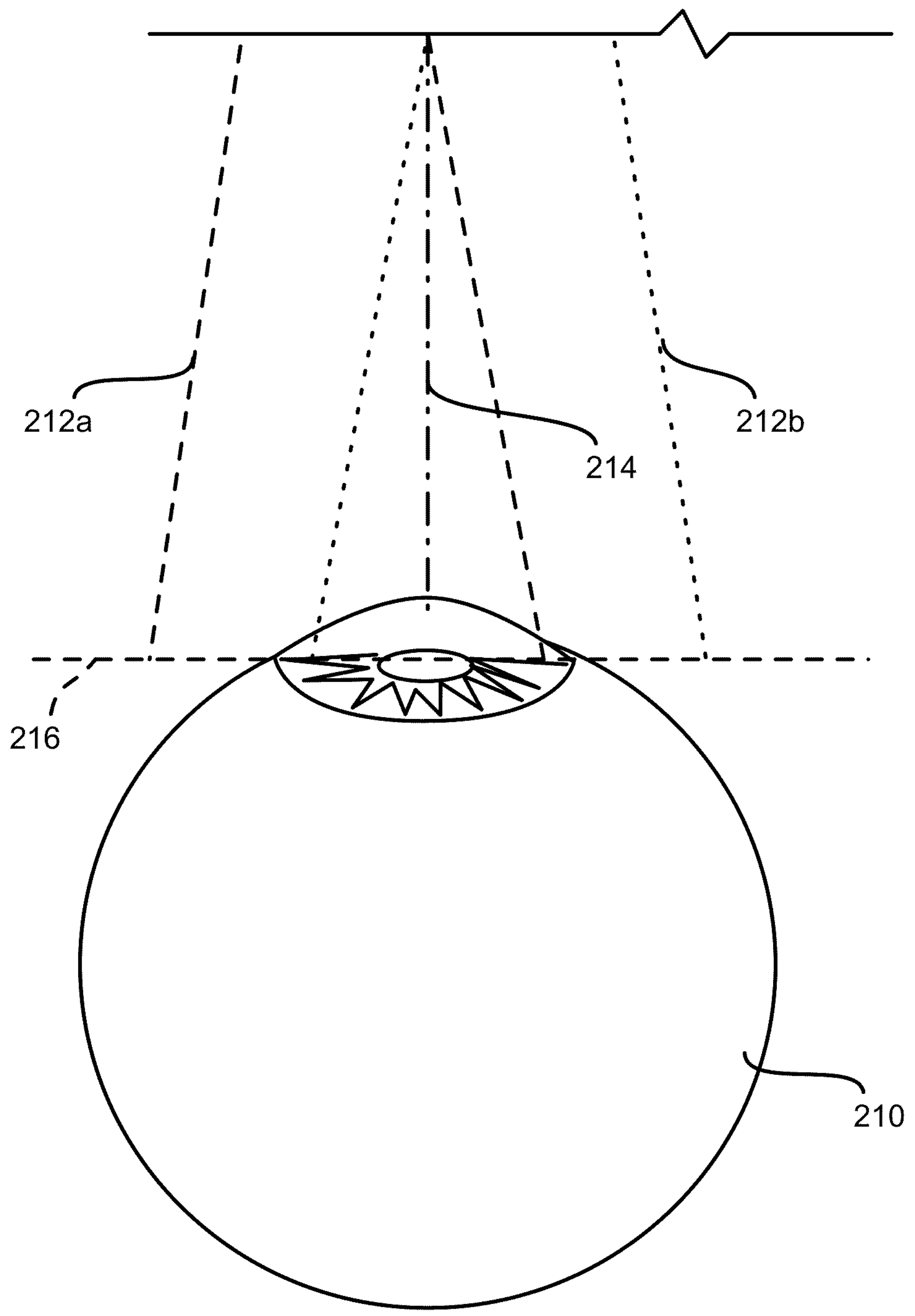
FIG. 3 illustrates beams from the tunable illumination source illuminating an eye in accordance with certain embodiments.
Figure 4:
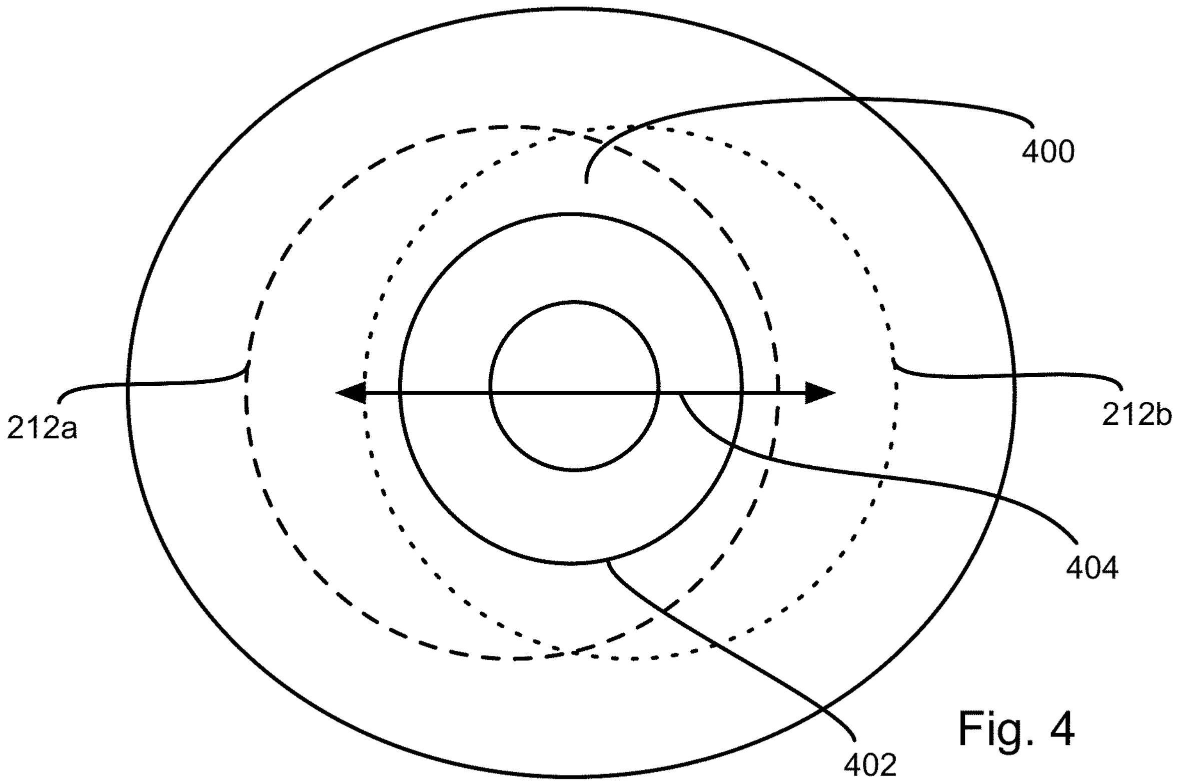
FIG. 4 illustrates the overlap between beams from the tunable illumination source illuminating the eye in accordance with certain embodiments.

Referring to FIGS. 3 and 4, the coaxial beams 212*a*, 212*b* may be incident on the eye such that the beams 212*a*, 212*b* only partially overlap in the corneal plane 216. For example, as shown in FIG. 4, the beams 212*a*, 212*b* may overlap over a region 400 that is at least as large as the limbus 402 of the eye 210, such as between 0.9 and 1.3 times the size of the limbus 402, along a direction 404 perpendicular to the optical axis and parallel to the offset direction between the coaxial beams 212*a*, 212*b*. The oblique beam 220 may overlap the entirety of the beams 212*a*, 212*b* in the corneal plane 216, such as being between 1 and 1.5 times the size of the combined beams 212*a*, 212*b* in the corneal plane 216.

Figure 5:
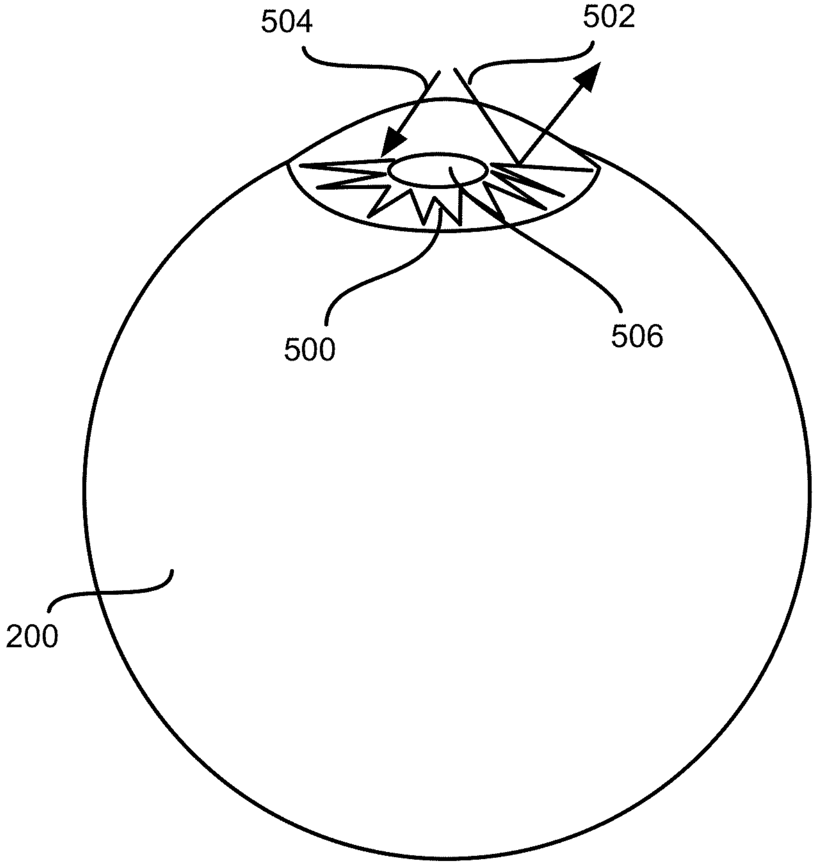
FIG. 5 illustrates the absorption and transmission of illumination from the iris of the eye in accordance with certain embodiments.
Figure 6:
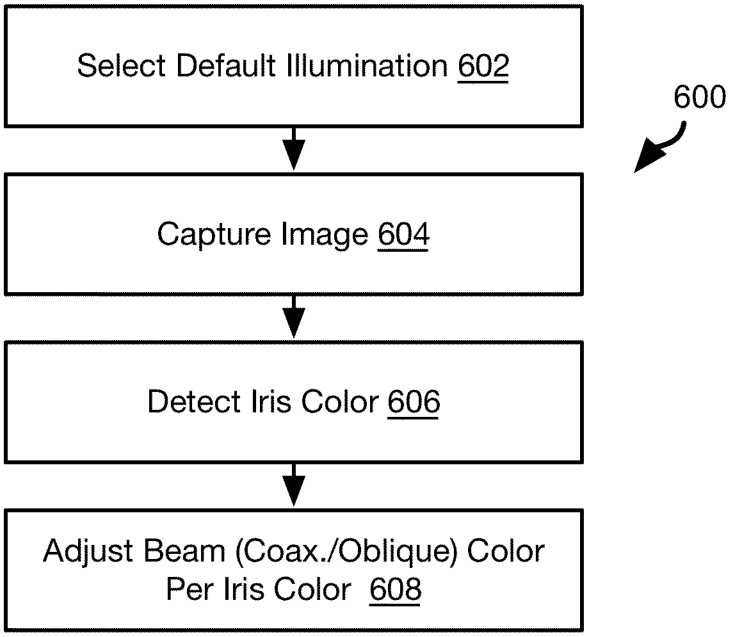
FIG. 6 is a process flow diagram of a method for illuminating the iris of the eye in accordance with certain embodiments.

Referring to FIGS. 5 and 6, the ability to independently control the color and intensity of the coaxial beams 212*a*, 212*b* and the oblique beam 220 may be used to reduce unwanted reflections during an ophthalmic treatment, such as reflection from the iris 500. For example, referring specifically to FIG. 5, light 502 incident on the iris 500 that is the same color as the iris will be reflected to a greater extent than light 504 that is a different color from the iris 500. Reflections from the iris may interfere with the ability to image portions of the eye 210 beyond the pupil 506, e.g., the retina, crystalline lens, vitreous, etc.

Referring specifically to FIG. 6, a method 600 performed by the controller 222 may include selecting, at step 602, default illumination parameters (e.g., color and intensity) for some or all of the coaxial beams 212*a*, 212*b* and oblique beam 220 and illuminating the eye 210 with light generated according to the default illumination parameters. The method 600 may include capturing, at step 604, an image of the eye 210 using the digital camera 108*b* while the eye 210 is illuminated according to the default illumination parameters. The image captured at step 604 may then be analyzed, at step 606, to identify one or more attributes of a representation of the eye 210 in the image, such as the representation of the iris 500 and detect the color of the iris 500. The method 600 may then include adjusting, at step 608, the color of some or all of the coaxial beams 212*a*, 212*b* and oblique beam 220 according to the detected color of the iris 500. For example, the color of some or all of the coaxial beams 212*a*, 212*b* and oblique beam 220 may be adjusted to be different than the color of the iris 500. In some applications, light incident on the retina, particularly red and near-infrared light will give rise to the red reflex such that notwithstanding selection of the illumination color to be different from that of the iris 500, the red reflex may provide appropriate illumination for the surgeon 106 to discern structures and features of the eye 210. For example, selecting an illumination color lacking blue or green for an iris that is blue or green reduces reflections from the iris while still providing red light which is suitable for inducing the red reflex.

Note that where the iris 500 itself is the object of an ophthalmic treatment, the opposite of the method 600 may be performed: the adjustment at step 608 may ensure that the light from some or all of the coaxial beams 212*a*, 212*b* and oblique beam 220 matches the color of the iris 500 in order to enhance reflections from the iris 500.

Figure 7:
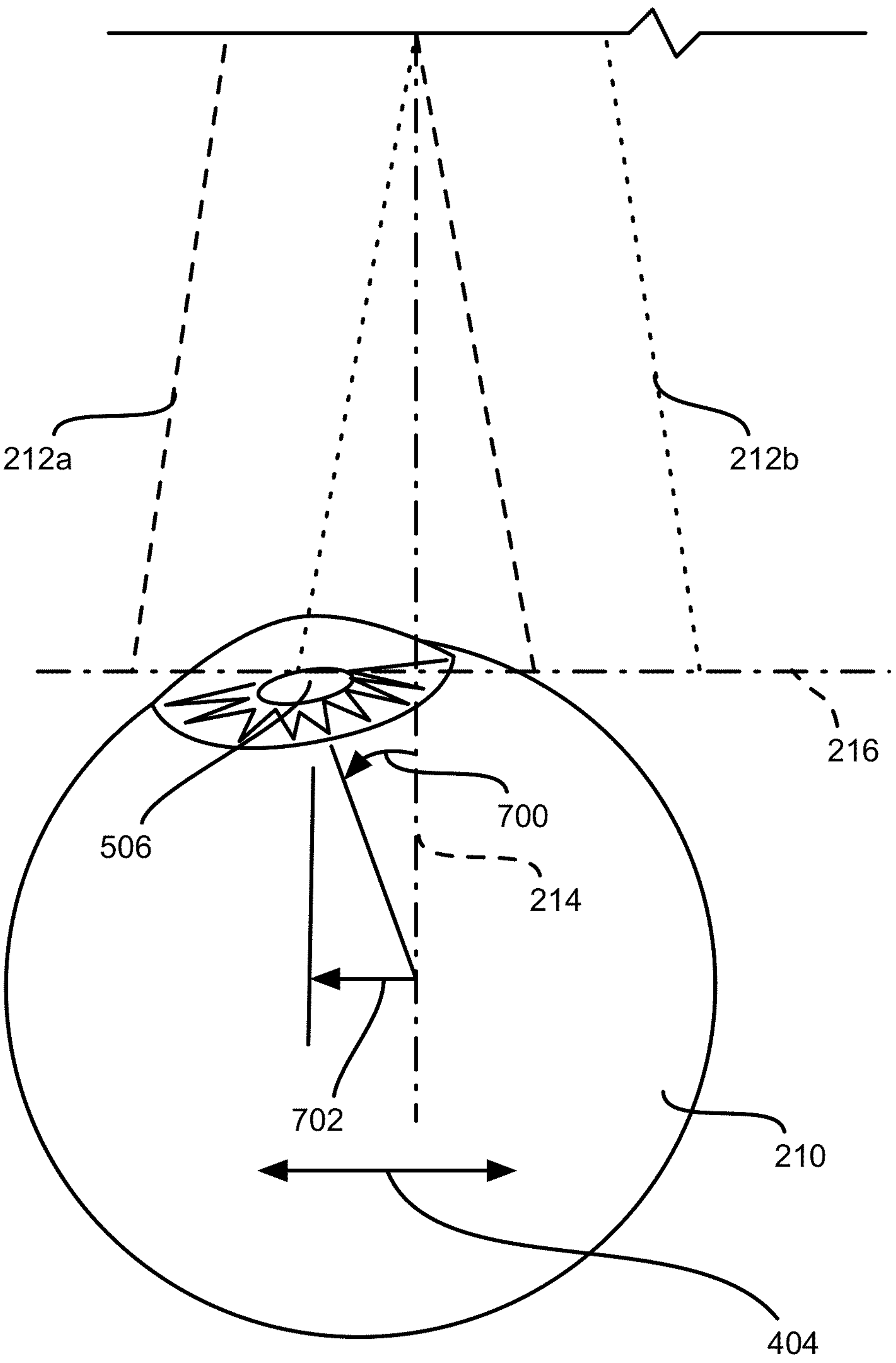
FIG. 7 illustrates possible misalignment of the eye with respect to an optical axis of the surgical microscope in accordance with certain embodiments.
Figure 8:
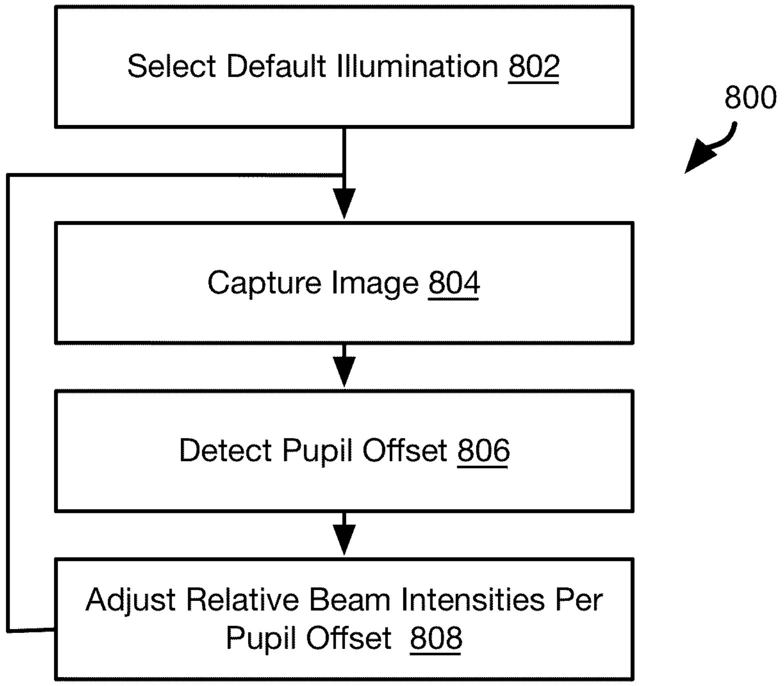
FIG. 8 is a process flow diagram of a method for compensating for misalignment of the eye using the tunable illumination source in accordance with certain embodiments.
Figure 9:
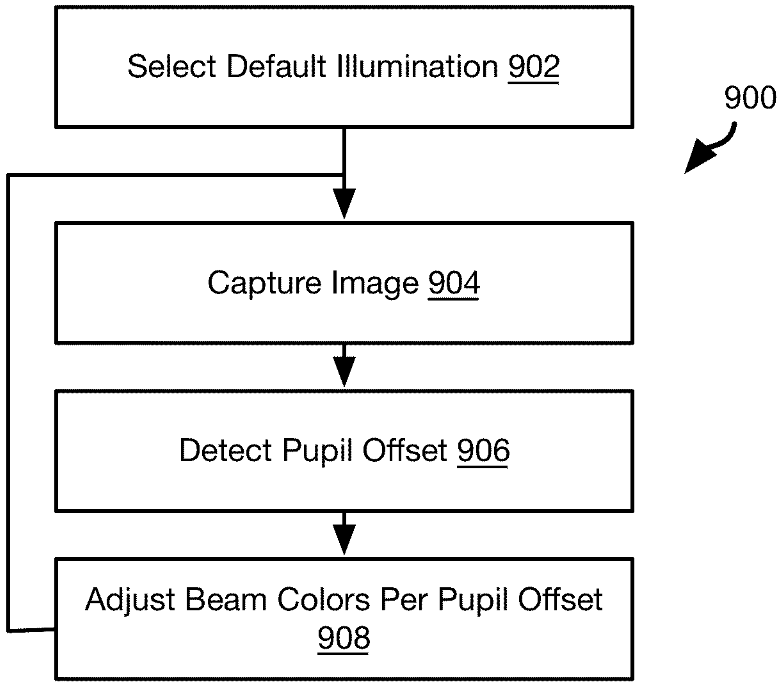
FIG. 9 is a process flow diagram of an alternative method for compensating for misalignment of the eye using the tunable illumination source in accordance with certain embodiments.

Referring to FIGS. 7, 8, and 9, during an ophthalmic treatment, the patient's eye 210 may move relative to the optical axis 214 of the surgical microscope 108. For example, the eye 210 may rotate an angle 700 relative to the optical axis 214 and/or translate a distance 702 from the optical axis 214 along direction 404. The ability to adjust the intensity and/or color of the coaxial beams 212*a*, 212*b* may be used to compensate for such rotation and translation, particularly components of such rotation and translation that are parallel to the direction 404 along which the coaxial beams 212*a*, 212*b* are offset from one another.

The intensity of each of the coaxial beams 212*a*, 212*b* and oblique beam 220 that reach the retina must be limited in order to avoid harming the retina, i.e., avoid "phototoxicity." In particular, the intensity of blue light for each beam must be maintained within safe levels. Since the coaxial beams 212*a*, 212*b* and oblique beam 220 may all define different angles relative to the optical axis 214 and the optical axis of the eye, the spots created on the retina by each beam 212*a*, 212*b*, 220 may not overlap such that the phototoxicity of each beam 212*a*, 212*b*, 220 may be controlled independently. However, where one or more of the spots of one or more beams 212*a*, 212*b*, 220 do overlap at the retina, the combined phototoxicity may then be controlled.

When the intensity of the coaxial beams 212*a*, 212*b* are equal, the amount of light from the coaxial beams 212*a*, 212*b* entering the eye 210 will also be approximately (e.g., within 1 percent) equal where the optical axis of the eye 210 is aligned with and parallel to the optical axis 214. However, in the case where the optical axis of the eye 210 is not aligned with and/or not parallel to the optical axis 214 the amount of light from the coaxial beams 212*a*, 212*b* entering the eye 210 will be unequal with the difference increasing with increase in the angle 700 and distance 702. Where the angle 700 and distance 702 are in the same direction, i.e., both contributing to the pupil 506 moving to the same side along direction 404, this inequality will be compounded. Where the angle 700 and distance 702 are in opposite directions, i.e., contributing to movement of the pupil 506 to different sides along direction 404, this inequality will be reduced.

Movement of the pupil 506 relative to the optical axis 214 having a component in the direction 404 will reduce the amount of light from one of the coaxial beams 212*a*, 212*b* that enters the pupil 506. For example, in the scenario of FIG. 7, the amount of light from coaxial beam 212*b* will be reduced due to movement of the pupil 506 away from the center of the coaxial beam 212*b* in the corneal plane 216. The amount of light from coaxial beam 212*a* entering the pupil 506 may remain substantially constant or may increase. While not illustrated, the amount of light from the oblique beam 220 may also increase or decrease in a similar or comparable manner. For example, movement of the pupil 506 away from the oblique optics 218 may reduce the amount of light entering the pupil from the oblique beam 220 and movement of the pupil 506 toward the oblique optics 218 may increase the amount of light entering the pupil from the oblique beam 220.

The intensity of some or all of the coaxial beams 212*a*, 212*b*, and oblique beam 220 may therefore be adjusted in response to movement of the pupil 506 having a component in direction 404 to cause the intensity of light reaching the retina as a result of the adjustment to be closer to the intensity of light reaching the retina when the pupil 506 is aligned with and parallel to the optical axis 214.

Referring specifically to FIG. 8, the illustrated method 800 may be used to compensate for movement of the pupil 506. The method 800 performed by the controller 222 and may include selecting, at step 802, default illumination parameters (e.g., color and intensity) for some or all of the coaxial beams 212*a*, 212*b* and oblique beam 220 and illuminating the eye 210 with light generated according to the default illumination parameters. The default illumination parameters may have equal intensities for the coaxial beams 212*a*, 212*b* and be selected such that for a range of possible angles 700 and distances 702, the amount of light reaching the pupil will be at safe levels.

The method 800 may include capturing, at step 804, an image of the eye 210 using the digital camera 108*b* while the eye 210 is illuminated according to the default illumination parameters. The image captured at step 804 may then be analyzed, at step 806, to identify one or more attributes of a representation of the eye 210 in the image. For example, step 806 may include identifying the representation of the pupil 506 and detect the offset of the pupil 506 from the optical axis 214. The offset may be a measure of a number of pixels (or a distance derived from the number of pixels) between a center of the representation of the pupil 506 in the image and a center of the image (or some other pixel position corresponding to the optical axis 214).

The method 800 may include adjusting, at step 808, intensities of one or both of the beams 212*a*, 212*b* according to the offset detected at step 806. For example, when the pupil 506 is aligned with the optical axis 214 (see FIG. 3), the coaxial beams 212*a*, 212*b* may each emit light at 50% of a maximum intensity. When the pupil 506 is offset from the optical axis (see FIG. 7) toward the center of the coaxial beam 212*a*, the intensity of coaxial beam 212*a* may be increased to 66% of the maximum intensity and the intensity of coaxial beam 212*b* may be decreased to 34% of the maximum intensity. For a greater offset toward the coaxial beam 212*a*, the intensity of coaxial beam 212*a* may be increased to 82% of the maximum intensity and the intensity of coaxial beam 212*b* may be decreased to 18% of the maximum intensity. For an even greater offset toward the coaxial beam 212*a*, the intensity of coaxial beam 212*a* may be increased to 98% of the maximum intensity and the intensity of coaxial beam 212*b* may be decreased to 2% of the maximum intensity. The intensities of the coaxial beams 212*a*, 212*b* may be selected such that the combined intensity of the coaxial beams 212*a*, 212*b* in regions that overlap in the corneal plane is equal to 100% of the maximum intensity of a single beam of the coaxial beams 212*a*, 212*b*.

Stated more generally, the intensity of a beam of the coaxial beams 212*a*, 212*b* may be set to Max+F(D), where D is the offset toward the beam and is negative if the offset is away from the beam. F( ) may be a function that increases with increasing D, such as multiplication by a scaling factor or some other function. In some embodiments, the intensity of each coaxial beam 212*a*, 212*b*, as a percentage of the maximum intensity of each coaxial beam 212*a*, 212*b*, may be calculated as 50*(1+D/Dmax), where Dmax is the maximum expected or compensable offset in either direction from the optical axis 214. Accordingly, for the left coaxial beam 212*a*, leftward movement toward the left coaxial beam 212*a* (positive D) by Dmax will result in 100 percent intensity and rightward movement away from the left coaxial beam 212*a* (negative D) by Dmax will result in 0 percent intensity. For the right coaxial beam 212*b*, rightward movement toward the right coaxial beam 212*b* (positive D) by Dmax will result in 100 percent intensity and leftward movement away from the right coaxial beam 212*b* (negative D) by Dmax will result in 0 percent intensity.

The method 800 may be repeated from step 804 periodically in order to compensate for changes in the offset of the pupil 506. For example, steps 804-808 may be repeated every 0.5 seconds, every 0.1 seconds, every 10 milliseconds, or some other interval. Following an initial iteration, the illumination parameters used at step 804 may be those selected according to step 808 of a preceding iteration.

Referring specifically to FIG. 9, the illustrated method 900 may be used to compensate for movement of the pupil 506 by changing the colors of the coaxial beams 212*a*, 212*b*. The method 900 performed by the controller 222 and may include selecting, at step 902, default illumination parameters (e.g., color and intensity) for some or all of the coaxial beams 212*a*, 212*b* and oblique beam 220 and illuminating the eye 210 with light generated according to the default illumination parameters. The default illumination parameters may have equal intensities for the coaxial beams 212*a*, 212*b* and be selected such that for a range of possible angles 700 and distances 702, the amount of light reaching the pupil will be at safe levels. In some embodiments, the default illumination parameters cause the generation of pink light, i.e., a mix of white and red light or light in which green and blue intensities are equal and the intensity of the red light is greater than the green and blue intensities. Pink light may have the advantage of providing abundant red light for simulating the red reflex with relatively less blue light to contribute toward phototoxicity.

The method 900 may include capturing, at step 904, an image of the eye 210 using the digital camera 108*b* while the eye 210 is illuminated according to the default illumination parameters. The image captured at step 904 may then be analyzed, at step 906, to identify one or more attributes of a representation of the eye 210 in the image. For example, step 906 may include identifying the representation of the pupil 506 and detect the offset of the pupil 506 from the optical axis 214. The offset may be a measure of a number of pixels (or a distance derived from the number of pixels) between a center of the representation of the pupil 506 in the image and a center of the image (or some other pixel position corresponding to the optical axis 214).

The method 900 may include adjusting, at step 908, colors of one or both of the beams 212*a*, 212*b* according to the offset detected at step 906. For example, when the pupil 506 is aligned with the optical axis 214 (see FIG. 3), the coaxial beams 212*a*, 212*b* may each emit light having the red component elevated, i.e., pink light. When the pupil 506 is offset from the optical axis (see FIG. 7) toward the center of the coaxial beam 212*a*, the red component of the coaxial beam 212*a* may be increased and the red component of the coaxial beam 212*b* may be decreased, in order to provide a more realistic white illumination color for illuminating the portion of the corneal plane illuminated by coaxial beam 212*b*.

Stated more generally, the intensity of the red component of a beam of the coaxial beams 212*a*, 212*b* may be set equal to $R_0$+F(D), where D is the offset toward the beam and is negative if the offset is away from the beam. $R_0$ may be a default intensity for the red component, such as 50% or less of a maximum intensity of the red component. F( ) may be a function that increases with increasing D, such as multiplication by a scaling factor or some other function. In some embodiments, the intensity of the red component of each coaxial beam 212*a*, 212*b* may be calculated as $R_0+R_1*(1+D/Dmax)$, where Dmax is as defined above and $R_1$ is less than or equal to $R_0/2$. Accordingly, for the left coaxial beam 212*a*, leftward movement toward the left coaxial beam 212*a* (positive D) by Dmax will result in an intensity of the red component being $R_0+2*R_1$ and rightward movement away from the left coaxial beam 212*a* (negative D) by Dmax will result in the intensity of the red component being $R_0-2*R_1$. For the right coaxial beam 212*b*, rightward movement toward the right coaxial beam 212*b* (positive D) by Dmax will result in the intensity of the red component being $R_0+2*R_1$ and leftward movement away from the right coaxial beam 212*b* (negative D) by Dmax will result in the intensity of the red component being $R_0-2*R_1$.

The green and blue components of each coaxial beam 212*a*, 212*b* may either (a) remain constant or (b) be reduced or increased in correspondence with the increase or decrease in the red component: $G_0$−F(D)/2, $B_0$−F(D)/2, where $G_0$ and $B_0$ are the default intensity levels for green and blue light. In some embodiments, the maximum reduction in intensity of the red component is to a point that the light from a beam 212*a*, 212*b* becomes white light, i.e., red, green, and blue components equal. In some embodiments, the maximum increase in intensity of the red component is to a point that the light from a beam 212*a*, 212*b* becomes pure red light, i.e., green and blue components at zero intensity and red component at maximum intensity or some other predefined maximum value.

The method 900 may be repeated from step 904 periodically in order to compensate for changes in the offset of the pupil 506. For example, steps 904-908 may be repeated every 0.5 seconds, every 0.1 seconds, every 10 milliseconds, or some other interval. Following an initial iteration, the illumination parameters used at step 904 may be those selected according to step 908 of a preceding iteration.

Note that the controller 222 may receive inputs from the input device 226 that specify the red component in each coaxial beam 212*a*, 212*b* and possibly the oblique beam 220. For example, a physical slider or rotating dial or a graphical user interface element implementing a slider or dial may be adjusted by the surgeon 106. For example, moving the slider or dial in one direction may increase the red component in one coaxial beam 212*a*, 212*b* while decreasing the red component of the other coaxial beam 212*b*, 212*a*. In this manner, the surgeon may manually compensate for misalignment of the pupil 506 with the optical axis 214.

The methods 800 and 900 provide the benefit of providing light where it is needed based on the current position and orientation of the eye 210, which can reduce power consumption. The methods 900 may be performed automatically by the controller 222 or may be manually performed by the surgeon 106 or other user. For example, the input device 226 may include a slider corresponding to offset of the eye 210, whether actual or as arbitrarily selected by the surgeon 106. A surgeon may therefore move the slider to specify an offset and direction and invoke corresponding adjustments to the intensities of the coaxial beams 212*a*, 212*b* according to one or both of the methods 800 and 900.

Figure 10:
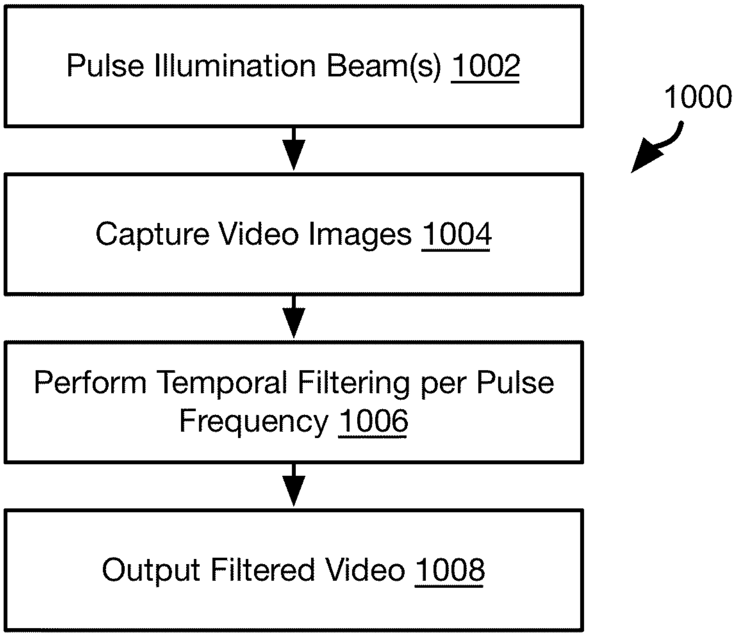
FIG. 10 is a process flow diagram of a method for removing reflections from ambient illumination using the tunable illumination source in accordance with certain embodiments.
Figure 11:
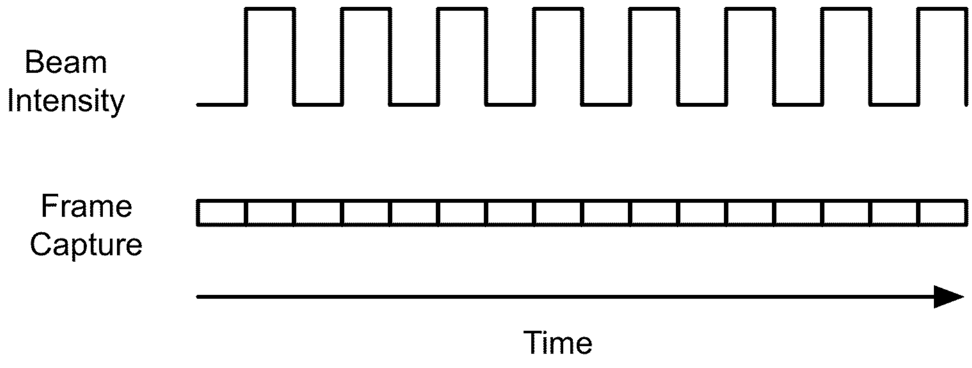
FIG. 11 is a timing diagram illustrating the pulsed emission of light from the tunable illumination source for removing reflections from ambient light in accordance with certain embodiments.

Referring to FIGS. 10 and 11, the tunable illumination source 200 may be used to reduce reflections from other light sources in the operating environment 100. For example, the method 1000 may include pulsing, at step 1002, some or all of the coaxial beams 212*a*, 212*b* and oblique beam 220 at a pulse frequency F. The pulses generated using some or all of the coaxial beams 212*a*, 212*b* and oblique beam 220 may be approximately square (see FIG. 11), i.e., an approximation of a square wave subject to limitations imposed by the frequency response of the light emitters 204 and of the control electronics of the illumination device 202.

The method 1000 further includes capturing, at step 1004, video images while some or all of the coaxial beams 212*a*, 212*b* and oblique beam 220 are pulsed. For example, as shown in FIG. 11, the frame rate at which video images are captured may be two times the pulse frequency F. In this manner, some video frames will be captured while some or all of the coaxial beams 212*a*, 212*b* and oblique beam 220 are pulsed on and at least some of the video frames will be captured while some or all of the coaxial beams 212*a*, 212*b* and oblique beam 220 are pulsed off.

The method 1000 further includes performing, at step 1006, temporal filtering according to the pulse frequency F. For example, for a given pixel position within the video images, the pixel values at that pixel position for all video images constitute a time series of values that may be temporally filtered to obtain filtered pixel values. Filtering may be performed using a digital bandpass filter with a center frequency of F. Accordingly, reflections from illumination sources that are not pulsed at the pulse frequency F will be attenuated. Video images including pixels resulting from the filtering of step 1006 may then be output at step 1008, such as to the display device 224 or to a storage device for subsequent viewing.

Figure 12:
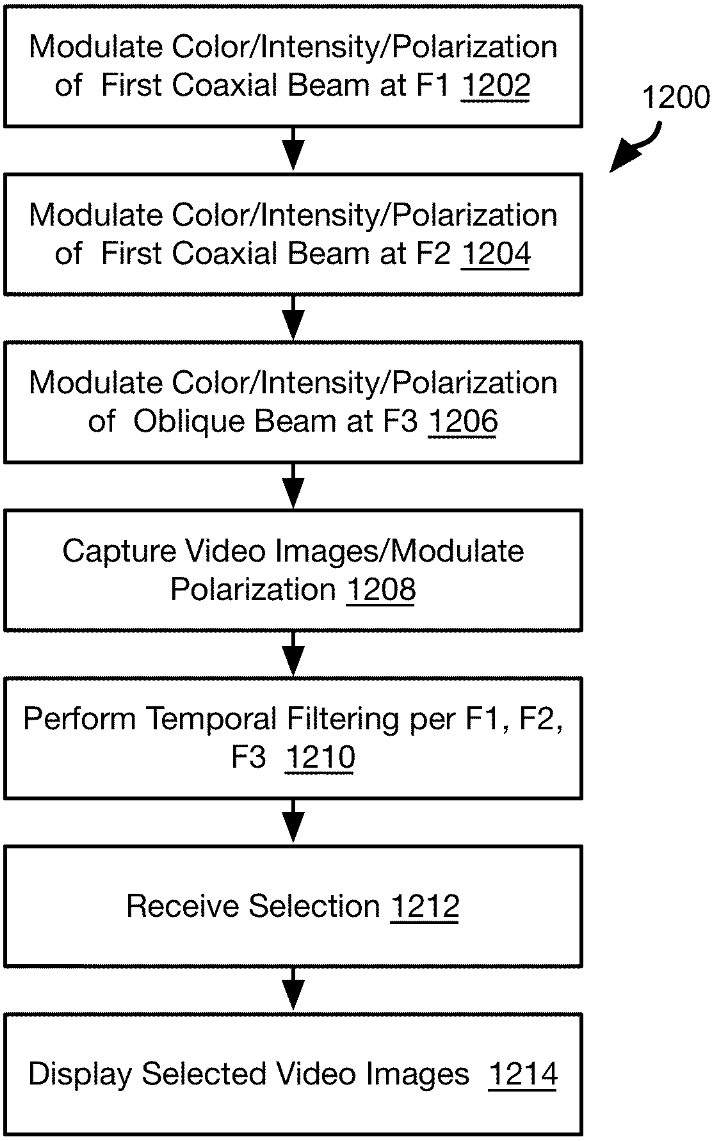
FIG. 12 is a process flow diagram of a method for capturing images with different illumination parameters in accordance with certain embodiments.

Referring to FIG. 12, the illustrated method 1200 may use the ability to independently control the color and intensity of each light emitter 204 along with the different angles of incidences of the beams 212*a*, 212*b*, 220 to enhance visibility of features of the eye 210. The method 1200 may presume that each light emitter 204 incorporates a polarizer capable of inducing a specific polarization in the output of each light emitter 204 or at least turning polarization on and off. Likewise, the coaxial illuminator optics 208 and/or optical microscope head 108*a* may incorporate the polarization filter 108*c* that likewise is tunable to a particular polarization angle or at least can be turned on and off. Capturing images with different illumination polarization and polarization filtering may likewise enable more detailed imaging of the anatomy of the eye 210.

The method 1200 may include modulating, at step 1202, some or all of the color, intensity, and polarization of the coaxial beam 212*a* at a frequency F1; modulating, at step 1204, some or all of the color, intensity, and polarization of the coaxial beam 212*b* at a frequency F2; modulating, at step 1206, some or all of the color, intensity, and polarization of the oblique beam 220 at a frequency F3. Note that less than all of steps 1202, 1204, 1206 may be performed. Steps 1202, 1204, 1206 may be performed simultaneously. The frequencies F1, F2, F3 may be identical or may all be unequal to one another. The frequencies F1, F2, F3 may be higher than the flicker fusion threshold of the human eye 210, e.g., at least 60 Hz. The modulation of steps 1202, 1204, 1206 may include generating approximately square wave pulses having the color, intensity, and/or polarization. The modulating of steps 1202, 1204, 1206 may be out of phase from one another and may have a duty cycle that is less than 50 percent. For example, a first frame of video captured with illumination by only a pulse of the coaxial beam 212*a*, a second frame captured with illumination by only a pulse of the coaxial beam 212*b*, and a third frame captured with illumination by only a pulse of the oblique beam 220. In other embodiments, pulses from multiple beams 212*a*, 212*b*, 220 are emitted simultaneously. The values for illumination parameters (color, intensity, polarization) may vary for the same beam 212*a*, 212*b*, 220 from one pulse to the next. Values for one or more parameters for a beam 212*a*, 212*b*, 220 may vary while others remain constant. For example, polarization may be modulated while color and/or intensity remain constant.

The method 1200 may include capturing, at step 1208, video images of the eye 210 while the eye 210 is illuminated according to some or all of steps 1202, 1204, and 1206. For example, one image may be captured for each pulse of each beam 212*a*, 212*b*, 220. Step 1208 may include modulating the polarization filter 108*c*. Modulating the polarization filter 108*c* may include modulating the angle of polarization and/or turning polarization on and off. For example, the polarization filter 108*c* may be modulated in synchronization with pulses of the beams 212*a*, 212*b*, 220. For example, during capture of a first frame, the polarization filter 108*c* may match the polarization of the coaxial beam 212*a* illuminating the eye 210 during capture of the first frame and, during capture of a second frame, the polarization filter 108*c* may match the polarization of the second coaxial beam 212*b* illuminating the eye 210 during capture of the second frame. This process may be repeated for each consecutive pair of frames. In some embodiments, during capture of a third frame contiguous with the first and second frames, the polarization filter 108*c* may match polarization of the oblique beam 220 illuminating the eye 210 during capture of the third frame. This process may be repeated for consecutive sets of three frames.

The method 1200 may include performing, at step 1210, temporal filtering according to some or all of the pulse frequencies F1, F2, and F3. Temporal filtering may be performed as described above with respect to step 1006 of the method 1000. In some embodiments, the frame rate of the digital camera 108*b* may be much higher than the flicker fusion threshold to permit filtering at multiple frequencies that are also higher than the flicker fusion threshold.

The method 1200 may include receiving, at step 1212, a selection of a lighting scenario. A lighting scenario may include a set of values including some or all of an identifier of a particular beam 212*a*, 212*b*, 220, a polarization angle, a color, and an intensity. In response to the selected scenario, the method 1200 may include displaying, at step 1214, one or more frames of the video images that were captured for the selected scenario. For example, frames captured while the eye 210 was illuminated with the first coaxial beam 212*a* having a first polarization.

The selection received at step 1212 may be received from a surgeon 106 through the input device 226. The selection received at step 1212 may be part of an automatic algorithm. For example, images according to various lighting scenarios may be deployed in a periodic sequence such that the visual cortex of the surgeon 106 can integrate the different information provided in images captured with illumination according to the various lighting scenarios.

In a first example application of the method 1200, first images of the video images are captured with illumination from the first coaxial beam 212*a* but not the second coaxial beam 212*b* and second images of the video images are captured with illumination from the second coaxial beam 212*b* but not the first coaxial beam 212*a*. Due to the different angles of the coaxial beams 212*a*, 212*b*, the first images and the second images may provide a different perception of the eye 210.

In a second example, color triads (red, green, and blue intensity values) for some or all of the beams 212*a*, 212*b*, 220 are varied at frequencies F1, F2, and F3 as defined above. The variation in color may be across the entire color gamut achievable using the light emitters 204 or some portion thereof. The video images may then be electronically filtered based on frequency as described above. A set of images for each color triad, e.g., images with illumination from each beam 212*a*, 212*b*, 220, may be displayed rapidly in sequence. For example, 10 sets of three images for 10 different color triads may be displayed over a short period, such as 10 seconds.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

The invention claimed is:

1. A system for performing ophthalmic treatments, the system comprising:

a surgical microscope configured to capture images of an eye of a patient and defining an optical axis;

an illumination source configured to emit a plurality of beams onto the eye of the patient at a plurality of angles relative to the optical axis; and a controller coupled to the surgical microscope and the illumination source, the controller configured to:

independently control values for illumination parameters for each beam of the plurality of beams to facilitate imaging of the eye of the patient;

process an image of the eye of the patient to determine an attribute or change in attribute of the eye of the patient; and select the values for the illumination parameters for the plurality of beams to compensate for an effect on a visual characteristic of the captured image caused by the determined attribute or the determined change in attribute of the eye of the patient.

2. The system of claim 1, wherein the illumination parameters include intensity.

3. The system of claim 1, wherein the illumination parameters include color.

4. The system of claim 1, wherein the illumination parameters include polarization.

5. The system of claim 1, wherein the controller is further configured to select the values for the illumination parameters to reduce phototoxicity to the eye of the patient as the compensation for the effect on the visual characteristic.

6. The system of claim 1, wherein the controller is further configured to select the values for the illumination parameters to increase a red reflex of the eye of the patient as the compensation for the effect on the visual characteristic.

7. The system of claim 1, wherein the controller is further configured to:

illuminate the eye using the plurality of beams at a first blue light intensity;

receive the image from the surgical microscope; and increase intensity of blue pixel values of the image to simulate illumination with blue light having a second blue light intensity greater than the first blue light intensity.

8. The system of claim 1, wherein the controller is further configured to:

process an image of the eye of the patient to determine an iris color of the eye of the patient; and select the values for the illumination parameters to reduce reflections from the iris color as the compensation for the effect on the visual characteristic.

9. The system of claim 1, wherein the controller is further configured to:

process an image of the eye of the patient to determine an offset of a pupil relative to the optical axis; and select the values for the illumination parameters to compensate for the offset of the pupil as the compensation for the effect on the visual characteristic.

10. The system of claim 9, wherein the plurality of beams includes a first beam and a second beam positioned on opposite sides of the optical axis and offset from the optical axis by less than 4 degrees.

11. The system of claim 10, wherein the controller is further configured to select the values for the illumination parameters to compensate for the offset by increasing intensity of the first beam of the plurality of beams toward which the pupil is offset and decreasing intensity of the second beam of the plurality of beams away from which the pupil is offset.

12. The system of claim 10, wherein the controller is further configured to select the values for the illumination parameters to compensate for the offset by increasing a red component of the first beam toward which the pupil is offset and decreasing a red component of the second beam away from which the pupil is offset.

13. The system of claim 10, wherein the first and second beams converge toward one another with distance from the surgical microscope.

14. The system of claim 10, wherein the plurality of beams includes a third beam offset from the optical axis by between 5 and 12 degrees.

15. The system of claim 1, wherein the controller is further configured to:

modulate the values for the illumination parameters for at least a portion of the plurality of beams at a modulation frequency;

temporally filter images received from the surgical microscope with a bandpass filter to obtain filtered images; and output the filtered images to a display device.

16. The system of claim 15, wherein the controller is further configured to modulate the values for the illumination parameters for the at least the portion of the plurality of beams by modulating intensity for the at least the portion of the plurality of beams.

17. The system of claim 15, wherein the controller is further configured to modulate the values for the illumination parameters for the at least the portion of the plurality of beams by modulating color for the at least the portion of the plurality of beams.

18. The system of claim 15, wherein the controller is further configured to modulate the values for the illumination parameters for the at least the portion of the plurality of beams by modulating polarization for the at least the portion of the plurality of beams.

19. The system of claim 1, wherein the controller is further configured to independently control the values for the illumination parameters for each beam of the plurality of beams according to inputs received from a user.

20. A method comprising:

receiving, by a controller, a first image from a surgical microscope;

processing, by the controller, the first image to determine one or more attributes of a representation of an eye of a patient or change in the one or more attributes in the first image;

selecting, by the controller, values for one or more illumination parameters to compensate for an effect on a visual characteristic of the captured image caused by the determined one or more attributes or the determined change in the one or more attributes in the eyes; and illuminating, by the controller, the eye of the patient according to the values for the one or more illumination parameters using a tunable illumination source;

wherein the one or more attributes include at least one of iris color and pupil offset relative to an optical axis of the surgical microscope.

* * * * *